United States Patent [19]
Lavigne

[11] Patent Number: 5,897,521
[45] Date of Patent: Apr. 27, 1999

[54] SINUSAL INTUBATION DEVICE

[75] Inventor: Francois Lavigne, Outremont, Canada

[73] Assignee: Medilyfe, Inc., Quebec, Canada

[21] Appl. No.: 08/885,975

[22] Filed: Jun. 30, 1997

[51] Int. Cl.[6] ..................................... A61M 5/00
[52] U.S. Cl. ................... 604/8; 623/10; 604/275
[58] Field of Search .............................. 604/8, 9, 10, 93, 604/174, 175, 264, 275, 328, 94; 623/10

[56] References Cited

U.S. PATENT DOCUMENTS

| | | |
|---|---|---|
| D. 258,531 | 3/1981 | Orsing . |
| 858,996 | 7/1907 | Lamport . |
| 2,099,127 | 11/1937 | Leech ........................ 128/208 |
| 2,431,587 | 11/1947 | Schnee . |
| 2,859,518 | 11/1958 | Cohn ............................. 32/33 |
| 3,363,629 | 1/1968 | Kuhn ........................... 128/351 |
| 3,599,642 | 8/1971 | Tindel ......................... 128/351 |
| 3,964,488 | 6/1976 | Ring ............................ 128/351 |
| 4,056,104 | 11/1977 | Jaffe ........................... 128/351 |
| 4,508,535 | 4/1985 | Joh et al. ................. 604/174 X |
| 4,643,716 | 2/1987 | Drach ............................. 604/8 |
| 4,964,850 | 10/1990 | Bouton et al. ................. 604/54 |
| 4,981,477 | 1/1991 | Schon et al. ................. 604/264 |
| 5,139,502 | 8/1992 | Berg et al. ................... 606/108 |
| 5,139,510 | 8/1992 | Goldsmith, III et al. ..... 606/196 |
| 5,245,992 | 9/1993 | Nye ......................... 128/200.26 |
| 5,246,455 | 9/1993 | Shikani ......................... 623/10 |
| 5,279,610 | 1/1994 | Park et al. ................... 604/264 |
| 5,342,296 | 8/1994 | Persson et al. ................ 604/49 |
| 5,456,714 | 10/1995 | Owen ........................ 604/8 X |
| 5,470,320 | 11/1995 | Tiefenbrun et al. ......... 604/174 |
| 5,477,852 | 12/1995 | Landis et al. ............ 128/207.18 |
| 5,601,594 | 2/1997 | Best ............................. 606/199 |
| 5,693,065 | 12/1997 | Rains, III ..................... 606/196 |

FOREIGN PATENT DOCUMENTS 1337104  9/1987  U.S.S.R. .

OTHER PUBLICATIONS

Tube de Meatotomie Moyenne de Shikani.

*Primary Examiner*—John G. Weiss
*Assistant Examiner*—Ki Yong O
*Attorney, Agent, or Firm*—Bourque & Associates P.A.

[57] ABSTRACT

An intubation device is used to intubate a body passageway or cavity, such as the maxillary sinus, by ventilating, draining, irrigating, medicating or otherwise treating the body cavity. The intubation device includes a flexible tube, for providing access to the cavity, and an anchoring member disposed at a distal end of the flexible tube, for anchoring the tube to a region of the cavity. The tube includes a curved portion proximate the distal end, and the anchoring member includes one or more flanges extending from the distal end. The curved portion of the tube and one of the flanges form a receiving region adapted to receive and conform to a wall in the body cavity, such as the wall of the maxillary sinus. The method of nasal intubation includes inserting the anchoring member and distal end of the tube through a hole formed in the wall of the maxillary sinus. The receiving region receives the sinus wall and the flanges are disposed against the interior sinus wall to comfortably anchor the tube within the maxillary sinus. The proximal end of the tube extends through the nostril of the patient, allowing the tube to be used to treat the maxillary sinus.

9 Claims, 2 Drawing Sheets

SINUSAL INTUBATION DEVICE

FIELD OF THE INVENTION

The present invention relates to tubes for medical applications and more particularly, to a sinusal intubation device for placement through the nasalairway into the sinus cavity for sinus treatment.

BACKGROUND OF THE INVENTION

Intubation devices, in general, are well known in the medical field. Tubes are often inserted into body passageways or cavities of a patient to ventilate, drain, and/or irrigate the cavity into which the tube is inserted. Continuing efforts are being made to design intubation devices that are easily and comfortably inserted into a patient, particularly when the tube must be left in place within the patient.

One medical use for an intubation device is in the treatment of maxillary sinusitis. Sinusitis is an inflammation of the sinuses caused, for example, by viruses, bacteria or an allergy. In the maxillary sinus, the inflammation causes an obstruction of the ostium or opening into the maxillary sinus and swelling of the lateral wall of the nose. To treat persistent sinusitis, the inflamed and obstructed maxillary sinus must be accessed for draining and irrigation.

According to one well known procedure known as antrotomy, the wall of the maxillary sinus is penetrated to allow the sinus to be treated. One way of penetrating the maxillary sinus is with an endoscopically guided trephine or rotating cutting tool. Following local anesthesia, an endoscope is inserted into the nasal cavity to observe the cavity and guide the cutting edge of the trephine to the desired location on the wall of the maxillary sinus, typically the thinnest bone surface. The cutting edge of the trephine is covered by a sheath known as a cannula to prevent mucosal irritation and bleeding. The cannula is used to raise the inferior turbinate bone, allowing the cutting edge of the trephine to access the wall of the maxillary sinus. The maxillary sinus can also be accessed by puncturing the sinus wall, although trephination is less painful and less disruptive.

Once the sinus wall has been penetrated, the endoscope is removed and the cannula is left in place to guide the intubation device into the cavity. Intubation allows the inflamed maxillary sinus to be drained, ventilated or irrigated. Intubation typically offers a rapid relief of pain and rhinorrhea, and prevents the need for further anesthesia and penetration through the sinus wall.

Existing intubation devices, however, still cause some discomfort and are also difficult to install and use. One type of existing tube must be fixed to the wall of the sinus by suturing which requires difficult surgical installation and causes discomfort to the patient. Other types of intubation devices are not accessible to the patient and do not allow the patient to perform their own irrigation. Conventional intubation devices are also not shaped and dimensioned to conform to the sinus wall and cavity and therefore cause discomfort and difficult breathing. Further, some existing intubation devices only allow drainage or irrigation of the sinus cavity and are not capable of allowing introducing medication into the maxillary sinus for treatment of sinusitis.

Accordingly, a need exists for an intubation device that is easily inserted into a maxillary sinus without suturing and with minimal discomfort to the patient. A need also exists for an intubation device designed to be comfortably left in place in the maxillary sinus, to be accessible by the patient or the surgeon without complex instrumentation, and to remain in place when breathing, sneezing, or blowing.

SUMMARY OF THE INVENTION

The present invention features an intubation device for intubating a body cavity. The intubation device comprises a flexible tube having a proximal end, a distal end, and a passageway extending from the proximal end to the distal end. The flexible tube also includes a generally curved portion proximate the distal end. An anchoring member is disposed at the distal end of the flexible tube, for anchoring the flexible tube to a region of the body cavity. The anchoring member includes one or more flanges extending from the distal end of the flexible tube. The flexible tube and the anchoring member are preferably formed as one piece from a polyethylene material or other flexible material suitable for medical use.

The flexible tube preferably includes a substantially straight portion extending from the curved portion and an angled portion extending from the substantially straight portion to the proximal end of the flexible tube. The curved portion of the flexible tube preferably has a radius of curvature in a range of about 3.1 mm.

One of the flanges preferably extends from the distal end of the flexible tube opposite the curved portion, to form a receiving region, for receiving a wall in the body cavity. The generally curved portion of the flexible tube includes an arcuate surface and the flange includes a substantially straight surface. The arcuate surface and the substantially straight surface form a receiving region adapted to receive and conform to a sinus wall in a sinus cavity.

One embodiment of the intubation device includes a first flange extending from the distal end of the flexible tube in a first direction and a second flange extending from the flexible tube in a second direction opposite the first direction. The first and second flanges have rounded ends and together form a generally elliptical shape. The first flange is preferably longer than the second flange and forms a receiving region.

A method of treating a maxillary sinus of a patient using the intubation device of the present invention comprises the steps of: penetrating a wall of the maxillary sinus of the patient to form a hole in the wall of the maxillary sinus; inserting the anchoring member and the distal end of the flexible tube through the hole in the maxillary sinus; positioning the anchoring member against a surface of the wall within the maxillary sinus; positioning a proximal end of the flexible tube proximate a nostril of the patient; and accessing the maxillary sinus through the flexible tube. According to one method, the step of accessing the maxillary sinus through the flexible tube includes introducing medication through the flexible tube into the maxillary sinus. Other methods include draining, irrigating, and/or ventilating the maxillary sinus through the flexible tube.

BRIEF DESCRIPTION OF THE DRAWINGS

These and other features and advantages of the present invention will be better understood by reading the following detailed description, taken together with the drawings wherein.

DETAILED DESCRIPTION OF THE PREFERRED EMBODIMENT

Figure 1:
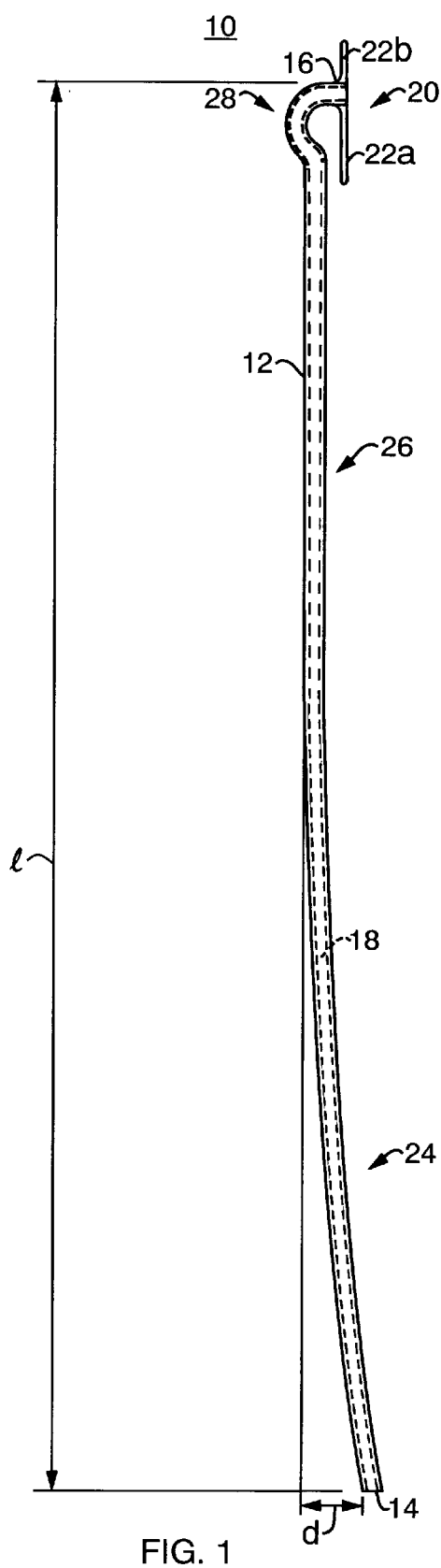
FIG. 1 is a side view of an intubation device according to the present invention.

An intubation device 10, FIG. 1, according to the present invention, is used to intubate a body passageway or cavity in a patient to allow ventilation, drainage, irrigation, the introduction of medication or the like. According to the exemplary embodiment, the intubation device 10 is used as a Maxillary Antrum Sinusostomy Tube (M.A.S.T.) to intubate a maxillary sinus or antrum through a patient's nasal airway cavity, as will be described in greater detail below. The present invention contemplates using the intubation device 10 or other similar devices having one or more features of the present invention in other similar body passageways or cavities, for example, in a patient's ear.

The intubation device 10 includes a flexible tube 12, preferably made of a flexible material, having a proximal end 14 and a distal end 16. A passageway 18 extends from the proximal end 14 to the distal end 16 of the tube 12, for providing access to the maxillary sinus or other cavity. An anchoring member 20 including one or more flanges 22a, 22b is disposed at the distal end 16 of the tube 12, for engaging with a region in the body cavity, such as the wall of the maxillary sinus. The tube 12 and anchoring member 20 are preferably formed as one piece from a polyethylene or other flexible material suitable for use in medical applications.

The preferred embodiment of the flexible tube 12 includes an angled portion 24 proximate the proximal end 14, a substantially straight intermediate portion 26, and a curved portion 28 disposed proximate the distal end 16. The angled portion 24 allows the tube 12 to be fit securely and comfortably in a nasal passage of a patient by adapting to the lateral wall of the nasal passageway under the inferior turbinate, as described in greater detail below.

According to one example of the intubation device 10 used as a M.A.S.T. to intubate a maxillary sinus, the length 1 of the tube 12 from the proximal end 14 to the distal 16 is approximately 100 mm. The angled portion 24 of the tube 12 extends off-axis from the substantially straight portion 26 of the tube 12 by a distance d of approximately 4 mm. In this example, the diameter of the passageway 18 is approximately 1.1 mm with a tube wall thickness of approximately 0.5 mm. The present invention contemplates other tube sizes and dimensions to accommodate nasal cavities or other types of cavities of various sizes.

Figure 2:
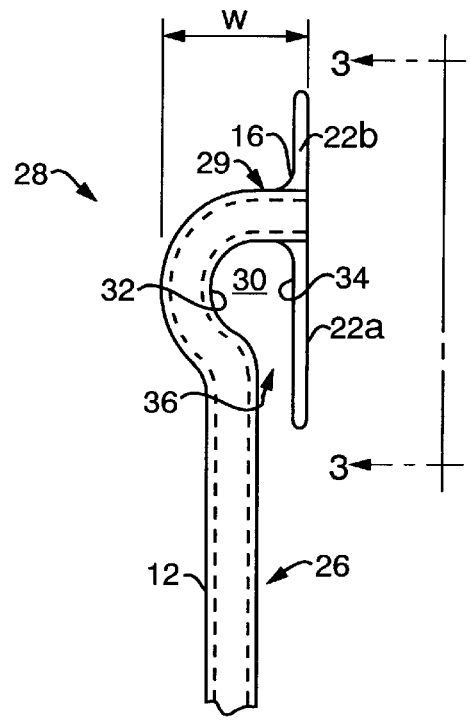
FIG. 2 is a close-up, partial side view of the distal end of the intubation device according to the present invention.

According to the preferred embodiment, the curved portion 28, FIG. 2, forms a receiving region 30 in cooperation with the at least one of the flanges 22a, for receiving and conforming to a wall in the cavity. The receiving region 30 is bounded in part by an arcuate surface 32 of the tube 12 and a substantially straight surface 34 of the flange 22. The flange 22 preferably extends from the distal end 16 generally parallel to the intermediate portion 26 of the tube 12 to form a space 36. The spacing 36 and receiving region 30 formed by the arcuate surface 32 and substantially straight surface 34 are particularly adapted to conform to the natural shape and thickness of the sinus wall and without disruption of the mucosal surface.

In one example, the space 36 is approximately 2.5 mm and the width w of the curved portion 28 is approximately 5.75 mm. One example of the curved portion 28 has a radius of curvature of about 3.1 mm. The flanges 22a, 22b are approximately 0.3 mm thick. The present invention contemplates other dimensions for the curved portion 28 to conform to sinus cavities of various sizes and with anatomical differences.

According to the preferred embodiment, a first flange 22a extends from the distal end 16 in one direction to form the receiving region 30. A second flange 22b extends from the distal end 16 in a second direction opposite the first direction. The second flange 22b and an upper portion 29 of the curved portion 28 of the tube 12 are adapted to engage a portion of the sinus wall opposite from the receiving region 30 when the distal end 16 has been inserted through a hole in the sinus wall.

Figure 3:
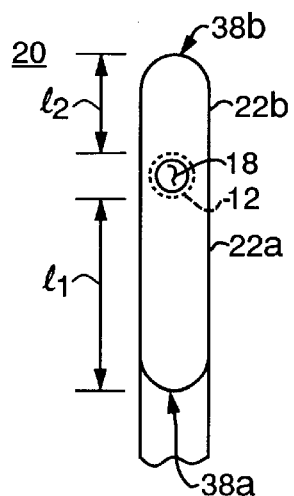
FIG. 3 is a front view of the anchoring member of the intubation device according to the present invention.
Figure 4:
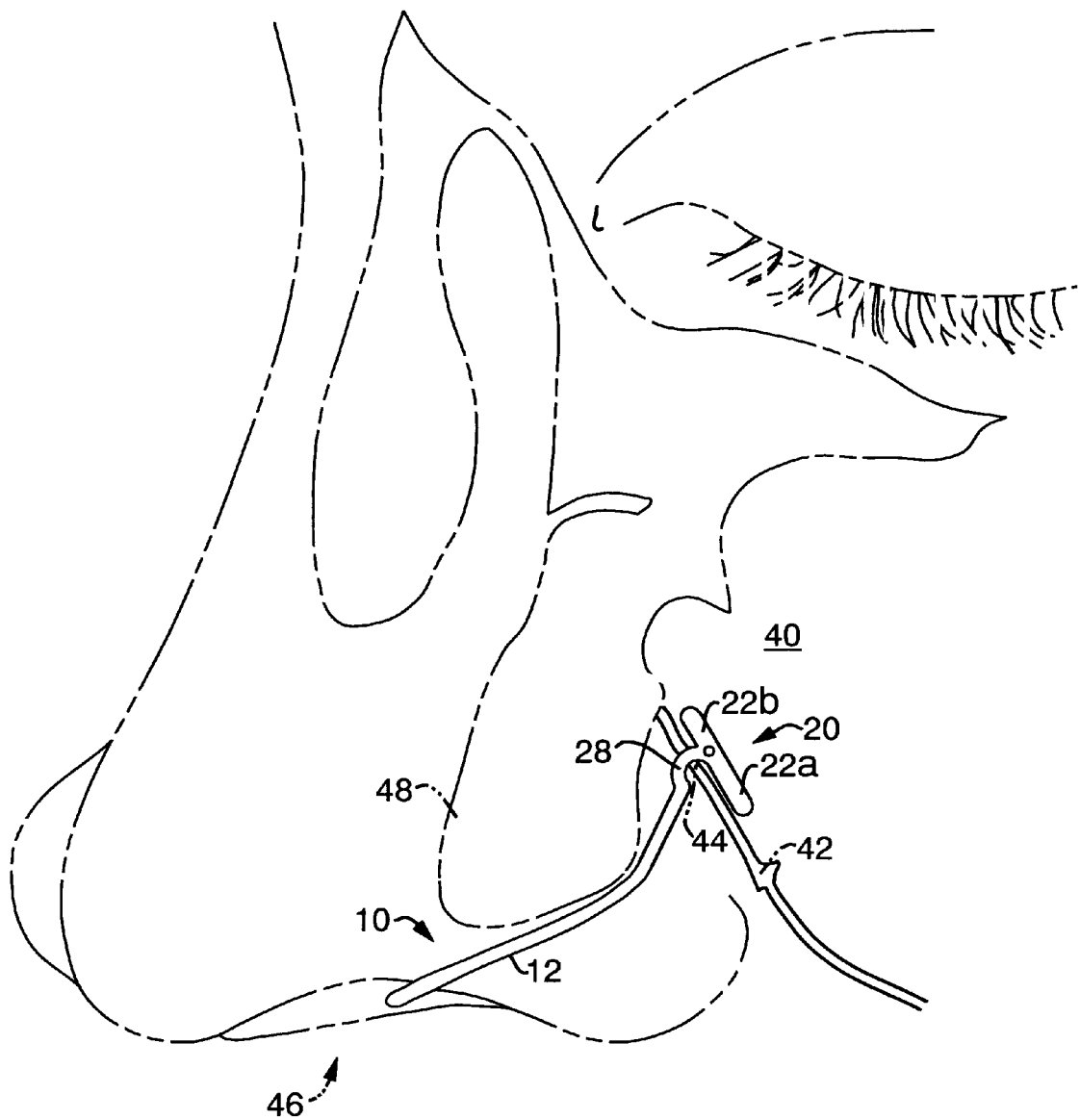
FIG. 4 is a schematic view of the intubation device disposed in the maxillary sinus of a patient, according to one application of the present invention.

According to the preferred embodiment of the anchoring member 20, FIG. 3, the first and second flanges 22a, 22b include rounded end regions 38a, 38b. The first flange 22a is preferably longer than the second flange 22b, for example, about twice as long. In one example, the first flange 22a extends from the tube 12 with a length $l_1$ of about 7 mm, and the second flange 22b extends from the tube 12 with a length $l_2$ of about 4 mm. The flanges 22a, 22b have a width of approximately 2.3 mm. The present invention contemplates other dimensions for the flanges 22a, 22b to accommodate sinus cavities of different anatomies.

In accordance with the exemplary use, the intubation device 10 is used as a M.A.S.T. to intubate a maxillary sinus 40 of a patient, allowing access to the maxillary sinus 40 through the tube 12. First, the sinus wall 42 is penetrated, for example, with an endoscopically guided trephine (not shown) that cuts or otherwise provides a hole 44 through the sinus wall 42. The intubation device 10 is then guided through the nasal region beneath the inferior turbinate bone 48. The anchoring member 20 is then inserted through the hole 44 formed in the sinus wall 42. Due to the flexibility of the flanges 22a and 22b, the flanges "fold" inwardly against the curved portion 28 when passing through the hole 44, and expand to their original position once the flanges clear the hole 44. The first and second flanges 22a, 22b are then positioned within the maxillary sinus 40 against the sinus wall 42 on either side of the hole 44.

The curved portion 28 in the tube 12 is comfortably disposed within the hole 44 with the sinus wall 42 received between the curved portion 28 and the flange 22a. The flanges 22a, 22b thereby comfortably anchor the tube 12 to the sinus wall 42 without suturing. The intubation device 10 can also be left comfortably in place while the flanges 22a, 22b prevent the tube 12 from being extruded as a result of breathing, sneezing, blowing, and/or treatment. This design of the intubation device 10 further eliminates excessive movement and prevents mucosal irritation.

The tube 12 extends through the nasal region of the patient to the nostril 46 so that both the doctor and the patient can use the tube 12 to treat the maxillary sinus region 40. In particular, the intubation device 10 of the present invention allows medications, such as steroids or antibiotics, to be introduced through the tube 12 and into the maxillary sinus. Other treatments of the maxillary sinus 40 include, but are not limited to, draining, ventilating, and irrigating the maxillary sinus 40.

Accordingly, the intubation device of the present invention is easily and comfortably inserted into the maxillary sinus of a patient and can be left in place for treatment of the sinus region by a doctor or the patient with minimal discomfort to the patient.

Modifications and substitutions by one of ordinary skill in the art are considered to be within the scope of the present invention which is not to be limited except by the claims which follow.

What is claimed is:

1. A nasal intubation device for intubating a maxillary sinus, said nasal intubation device comprising:

a flexible tube having a proximal end, a distal end, and a passageway extending from said proximal end to said distal end, for providing access to said maxillary sinus, said flexible tube including a generally curved portion proximate said distal end; and an anchoring member disposed at said distal end of said flexible tube, for anchoring said flexible tube to a region of said maxillary sinus, said anchoring member including:

at least first and second flanges extending generally orthogonally from said distal end of said flexible tube, wherein one of said at least first and second flanges and said curved portion of said flexible tube form a receiving region adapted to receive a wall of said maxillary sinus, and wherein said at least first and second flanges are adapted to engage a surface of said wall within said maxillary sinus to anchor said flexible tube.

2. The intubation device of claim 1 wherein said flexible tube includes a substantially straight portion extending from said curved portion.

3. The intubation device of claim 2 wherein said flexible tube includes an angled portion extending from said substantially straight portion to said proximal end of said flexible tube.

4. The intubation device of claim 1 wherein said curved portion of said flexible tube has a radius of curvature in a range of about 3.1 mm.

5. The intubation device of claim wherein said first flange extends from said distal end of said flexible tube in a first direction, and said second flange extends from said distal end of said flexible tube in a second direction opposite said first direction.

6. The intubation device of claim 8 wherein said first flange and said second flange have a generally elliptical shape.

7. The intubation device of claim 8 wherein said first flange is longer than said second flange.

8. The intubation device of claim 7 wherein said receiving region is formed by said first flange and said curved portion of said flexible tube.

9. The intubation device of claim 1 wherein said flexible tube and said anchoring member are formed as one-piece from a flexible material suitable for medical use.

* * * * *